United States Patent [19]

Hutson

[11] 4,391,777

[45] Jul. 5, 1983

[54] APPARATUS FOR MEASURING BREATH ALCOHOL

[75] Inventor: Donald G. Hutson, El Cerrito, Calif.

[73] Assignee: Cal Detect, Inc., Richmond, Calif.

[21] Appl. No.: 228,121

[22] Filed: Jan. 26, 1981

[51] Int. Cl.³ .................... G01N 1/22; G01N 21/62; G01N 27/04

[52] U.S. Cl. .................. 422/84; 73/864.83; 250/343; 422/90; 422/93; 422/98; 436/132; 436/151; 436/900

[58] Field of Search ............... 422/84, 85, 93; 23/907, 23/232 E, 230 M, 232 R; 73/1 G, 23, 864.83, 863.83; 250/343, 344, 345; 128/724, 725, 719; 324/715 N, 71 R

[56] References Cited

U.S. PATENT DOCUMENTS

| | | | |
|---|---|---|---|
| 3,476,516 | 11/1969 | Curry | 422/85 |
| 3,645,133 | 2/1972 | Sineth et al. | 73/204 |
| 3,830,630 | 8/1974 | Kiefer et al. | 23/232 E |
| 3,962,917 | 6/1976 | Terada | 128/724 |
| 4,090,078 | 5/1978 | Heim | 250/343 |
| 4,163,383 | 8/1979 | Vander Syde et al. | 422/84 |
| 4,268,751 | 5/1981 | Fritzler et al. | 250/343 |
| 4,278,636 | 7/1981 | Voigt et al. | 422/84 |
| 4,317,453 | 3/1982 | Heim | 422/84 |

FOREIGN PATENT DOCUMENTS

52-11088  7/1975  Japan .................... 73/1 G

*Primary Examiner*—Michael S. Marcus
*Attorney, Agent, or Firm*—Polster, Polster and Lucchesi

[57] ABSTRACT

A method of measuring breath alcohol includes blowing breath in a stream through an inlet line, hence through an orifice, past a thermistor exposed to the stream, changing the temperature of the thermistor to a predetermined temperature in response to a predetermined volume of breath. The thermistor provides an output signal to trigger the measurement of alcohol in the breath by an alcohol detecting device. The method and apparatus permit the purging of the system to provide a base line reference for the alcohol detection device, then testing to ensure that the breath inlet line is clear of contamination, then running an alcohol standard sample through the alcohol detecting device, again purging the system, again testing to ensure that the breath inlet line is clear of contamination, recording the result as a blank test, and thereafter blowing breath through the inlet line to obtain a demonstratably accurate measurement of breath alcohol.

1 Claim, 8 Drawing Figures

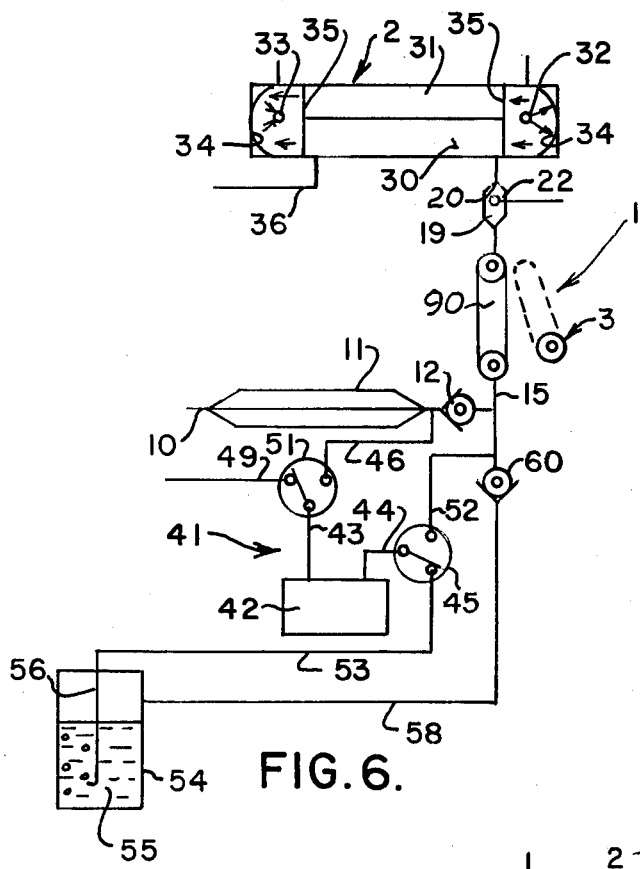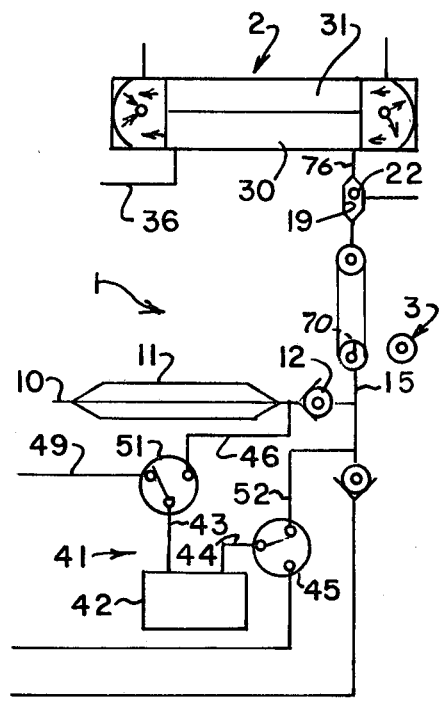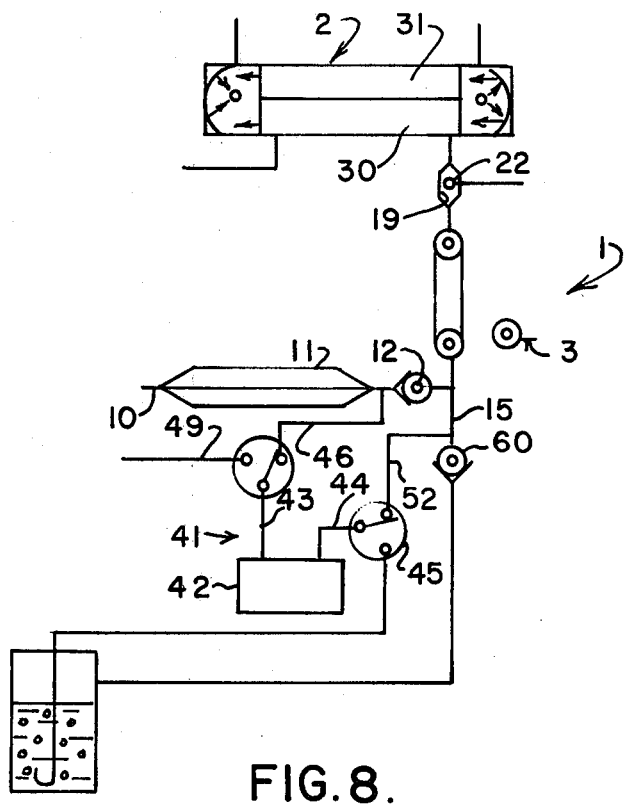

APPARATUS FOR MEASURING BREATH ALCOHOL

BACKGROUND OF THE INVENTION

Methods for measuring the alcohol content of a subject's expired breath to determine the alcohol concentration in the subject's blood are based on the proposition that alveolar air from the lungs has an alcohol content that is in equilibrium with the alcohol content of the blood. Only deep lung air will give an accurate measure, and, therefore, some means must be established to make sure that air in the mouth and upper respiratory tract has been discarded before making the measurement.

With infrared (IR) alcohol detectors now in commercial use, the subject has been required to blow at a minimum velocity and to sustain that velocity for a predetermined length of time before the IR measurement is made. This arrangement ensures that all subjects must deliver at least a minimum volume before the test will be valid. A problem with this method, is that a person who blows very hard may expire the predetermined minimum volume, generally considered to be about 800 to 1000 cc., before the time interval has elapsed. The problem is aggravated if the instrument's breath inlet system has a small resistance to the subject's expelling his breath. Subjects with small lung capacity can therefore deliver a desired minimum volume by blowing hard in less than the required time interval, so that the measurement is not triggered, and yet still be delivering deep lung air at the end of their exhalation. Thus, the same volume of air may be delivered over two different time intervals, but in many conventional devices, because of the use of a timing mechanism, a sample from the breath of a person with small lung capacity, who blows hard, may in effect be rejected. Although the measure of breath sample is sometimes expressed in terms of velocity, this would be interchangeable with pressure if the breath inlet system has a fixed restriction, because a particular velocity would require a given pressure at the inlet.

As shown in FIG. 1, the output of an IR instrument in response to breath samples delivered at a high pressure (A) and at low pressure (B) will reach the same final value. Accordingly, a determination of breath volume, without the requirement that it be delivered over a certain time interval is a desirable feature to establish the minimum requirement for completing breath alcohol measurement.

It is also highly desirable for evidentiary purposes to establish a base line, an alcohol standard, and a blank test record at each breath test.

One of the objects of this invention is to provide apparatus and method for measuring volume of a breath sample to trigger measurement of the alcohol content by an alcohol detector, without regard to time interval.

Another object is to provide an instrument the measurement of alcohol of which is of highly reliable evidentiary value.

Other objects will become apparent to those skilled in the art in the light of the following description and accompanying drawing.

SUMMARY OF THE INVENTION

In accordance with this invention, generally stated, a method of measuring breath alcohol and apparatus for carrying out the method are provided, wherein the breath is blown in a stream through an inlet line, thence through an orifice, past a thermistor exposed to the stream. The temperature of the thermistor is different from, in the preferred embodiment, above, the temperature of the breath. The temperature of the thermistor is changed by a predetermined amount to provide an output signal that is a function of the volume of breath sample passing the thermistor, which triggers the measurement of alcohol in the breath sample by an alcohol detecting device. The apparatus preferably also includes means for purging the system and establishing a base line reference; then testing the breath inlet line for contamination and if none is detected, recording the result as a blank test; thereafter running a standard alcohol sample through the detector to establish that it is operating correctly; again purging the system, running the blank test, and then admitting the breath sample from the subject.

BRIEF DESCRIPTION OF THE DRAWINGS

In the drawing.

FIG. 6 is a diagrammatic view of one embodiment of apparatus of this invention in position to run an alcohol standard or a breath sample;

FIG. 7 is a view of the apparatus of FIG. 6 in position to purge the system; and FIG. 8 is a diagrammatic view of the apparatus of FIGS. 6 and 7 in position to run a blank.

DESCRIPTION OF THE PREFERRED EMBODIMENT

Figure 1:
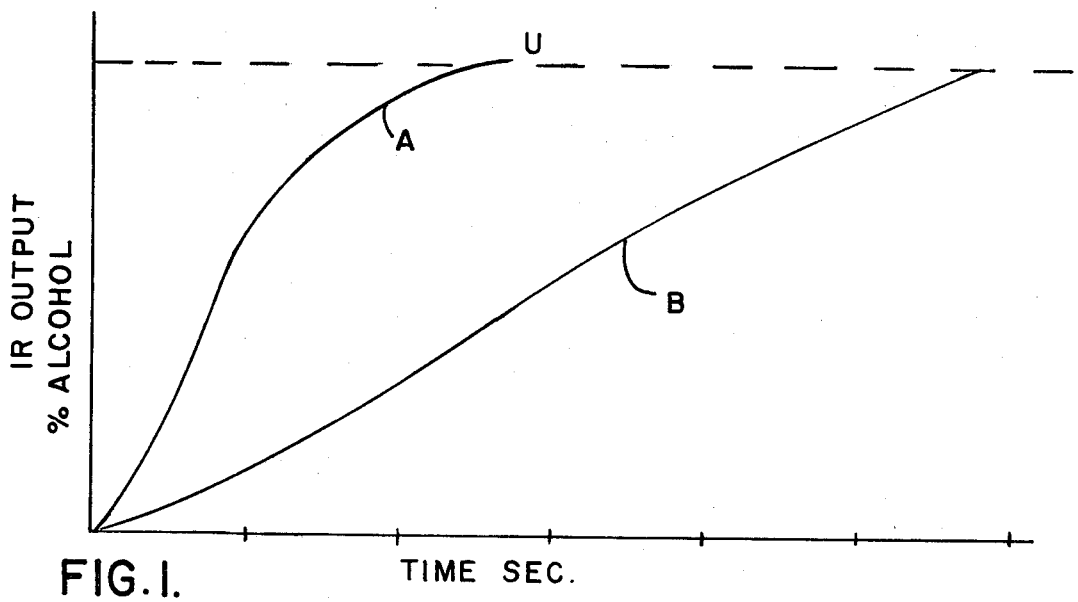
FIG. 1 is a graph showing the response of an IR detector to alcohol concentration in breath from a small lunged subject blowing hard, and a large lunged subject blowing at moderate pressure.
Figure 2:
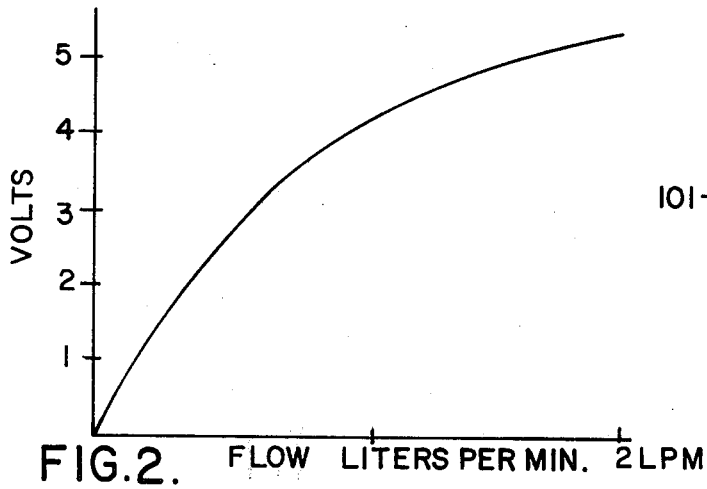
FIG. 2 is a graph showing thermistor response in volts against flow of breath in liters per minute.

Referring now to the drawing, and particularly to FIGS. 6 through 8, for one illustrative embodiment of apparatus of this invention, reference numeral 1 indicates a complete system, which in this embodiment includes an IR detector 2 and a semiconductor (SC) detector 3 as the alcohol detecting and measuring devices. The operation of the SC detector in combination with the IR detector, and the details of the sampling system by which the cooperation of the two detectors is accomplished is the subject of my co-pending application Ser. No. 228,119 filed concurrently herewith now U.S. Pat. No. 4,363,635.

The basic elements of the detection portion of the apparatus include a breath inlet line 10 surrounded through a portion of its length by a heater 11. The free end of the breath inlet line 10 is adapted to receive a mouthpiece or tube by which breath is introduced in a conventional manner. A breath inlet check valve 12 communicates on its inlet side with the breath inlet line, and on its outlet side with a sample inlet conduit 15. The sample inlet conduit 15 communicates, by way of an inlet passage 70, with one end of a sampling arm channel 90, which in turn communicates with an orifice chamber 19, with an orifice 20. A thermistor 22 projects into the orifice chamber. The orifice chamber 19 communicates, through the orifice 20 and an outlet passage 76, with a sample chamber 30 of the IR detector 2, which is vented to the atmosphere through a vent pipe 36.

The IR detector 2 is conventional, with a reference chamber 31, an IR source 32 at one end, an IR detector 33 at the other end, mirrors 34 and windows 35.

Reference numeral 41 indicates the blank, purge and test section of the system 1. The section 41 includes an air pump 42 with a suction line 43 and a pressure line 44. A 2-way solenoid operated suction valve 51 in the line 43 is constructed to connect the suction line 43 selectively to a test line 46, which communicates with the breath inlet line 11 between the heater and the inlet side of the check valve 12, in one position, and with an atmosphere line 49, in its other position. The pressure line 44 communicates with a solenoid operated 2-way pressure valve 45, selectively communicates with a purge line 52 and a container line 53.

The container line 53 communicates with a bubbler tube 56 which extends beneath the surface of a standard alcohol-water solution 55 in a container 54. Above the level of the alcohol-water solution 55, a standard sample line 58 communicates at one end with the interior of the container 54. At its other end, the standard sample line 58 communicates with the inlet side of an alcohol standard check valve 60, the outlet side of which communicates with the sample inlet conduit 15. The purge line 52 connects with the sample inlet conduit 15 between the check valve 60 and the breath inlet check valve 12.

Figure 4:
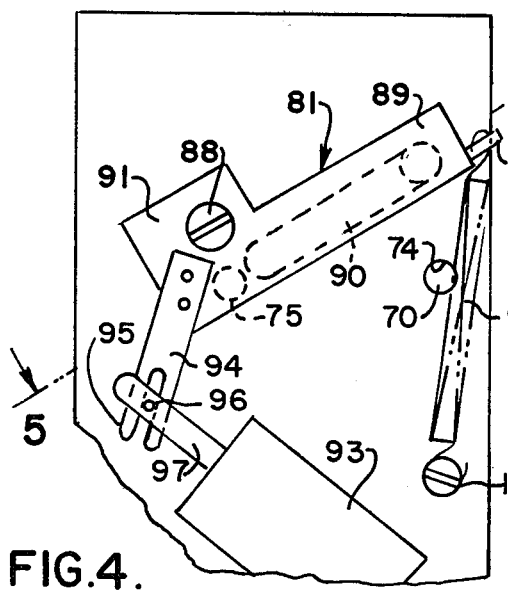
FIG. 4 is a top plan view of a sampling device of this invention.
Figure 5:
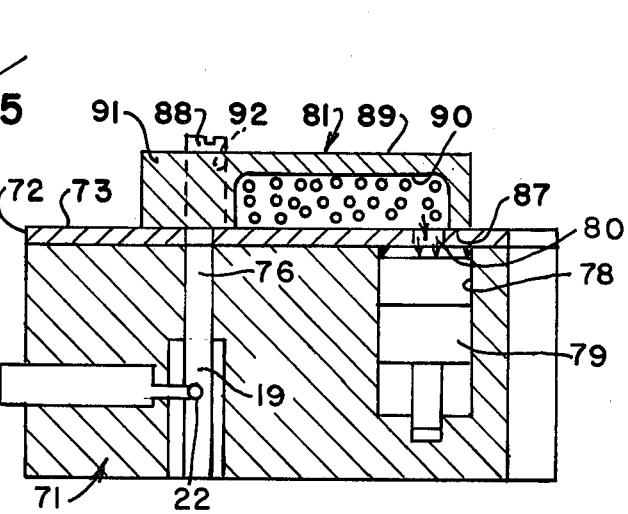
FIG. 5 is a sectional view taken along the line 5—5 of FIG. 4.

Although a description of the SC detector system and its use is set out in detail in my co-pending application, for completeness, the following is a description of the sampling system. Reference numeral 71 indicates a block, with the breath inlet passage 70 and the breath outlet passage 76 in it. The block 71 has a cover plate 72 with a smooth flat upper surface 73. The inlet passage 70 extends through the cover plate in an inlet port 74, and the outlet passage extends through the cover plate 72 in an outlet port 75. An SC detector cell 79 is mounted in a socket 78 in the body 71, communicating with a restricted port 80 in the cover plate 72. An L-shaped arm 81, with a flat bottom surface 87 is mounted for sliding engagement with the surface 73 on a pivot post 88, extending through a knuckle hole 92 in a foot portion 91 of the arm 81. An elongated stem 89 of the arm 81 has on its undersurface a blind channel 90, which in one position communicates with the inlet port 74 and outlet port 75, and in another position, as shown in FIGS. 4 and 5, with only the restricted port 80. In the latter position, the outlet port 75 is blocked and the inlet port 74 is open to the atmosphere. The arm has a bracket 94 projecting at an angle from the junction of the stem 89 and foot 91. The bracket 94 has a yoke 95, in which an actuating pin 96 extends and slides. The actuating pin 96 projects from an actuating rod 97 that is reciprocated by a solenoid coil 93. At the free end of the stem 89, an eye 98 projects. One end of a helical spring 99 is connected to the eye 98, and its other end, to a retaining pin 100.

Figure 3:
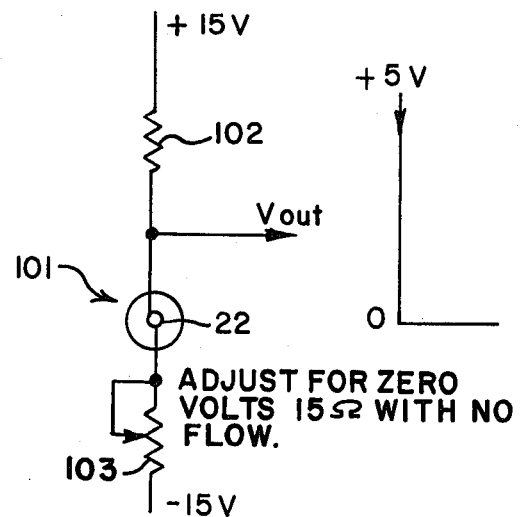
FIG. 3 is a fragmentary schematic view of a thermistor circuit.

In operation, the thermistor 22 is operated in the self-heating mode. The heater 11 is so constructed and arranged as to produce in a breath sample a uniform temperature, as it leaves the heated area, lower than the temperature of the thermistor. The output signal from the thermistor is linearized so that the voltage output is proportional to the breath velocity. This voltage is then integrated with respect to time and properly scaled to indicate the volume of breath that has passed through the orifice area. The thermistor circuit is shown fragmentarily and somewhat diagrammatically in FIG. 3. It includes a voltage adjusting system, with a resistor 102 and a variable resistor 103, the operation of which is self-evident. It operates on the principle that the thermistor resistance decreases with increasing temperature. In the quiescent state, current through the thermistor heats the thermistor, which decreases its resistance and thus lowers the voltage across the thermistor. As a breath sample passes over the thermistor, it provides a cooling effect, which increases the thermistor resistance, causing the voltage across the thermistor to increase. The higher the velocity, the more the cooling effect, and the higher the output voltage. The output voltage is fed to an analog-to-digital converter where the voltage is converted to a digital signal. The digital signal is then processed by a microprocessor computer, where the reading is linearized and integrated with respect to time. Once the minimum volume has been established, the output of the IR detector is computed and a reading is taken when it reaches its maximum value. As described in my co-pending application, when the maximum value is reached, the SC detector sampler is actuated, as indicated schematically in FIG. 8.

The IR detector measures the absorption of alcohol in the 3.39 micron region. The overall IR detector, including the electronics, has a response time of less than 0.25 seconds from zero to 90% of the final value.

The breath inlet check valve 12 prevents the subject from withdrawing the breath in the IR chamber.

The preferred complete test sequence is as follows. Air pump 42 is started and the solenoid operated valves 45 and 51 are moved to the positions shown in FIG. 7. In this position, air is drawn from the atmosphere through the line 49 and pumped through the sample inlet conduit, arm passage, orifice chamber and sample chamber, and out the vent pipe 36, to purge the system. The check valve 12 prevents the air from going through the breath inlet line 10, and the check valve 60, from going through the sample line 58. The purging of the system with fresh atmospheric air provides a base line reference for the IR detector.

The solenoid controlling the valve 51 is then actuated to move the valve 51 to the position shown in FIG. 8, in which condition of the system, the pump 42 sucks air through the breath inlet line 10, and test line 46, and forces it through the sample inlet conduit 15, arm passage 90, orifice chamber 19, sample chamber 30, and vent pipe 36. If during this step, any alcohol (or acetone) is present, it will be detected by the IR detector, and read out. Under those circumstances, the inlet line will need to be purged of contaminants and another blank run. If no contaminant is detected, the results are recorded as a blank test.

The solenoids operating both valves 49 and 51 are then energized to move the valves to the position shown in FIG. 6. In this position, air is sucked into the pump 42 through the line 49, and forced through the bubbler tube 56, thence through the sample line 58, past the check valve 60, through the sample inlet conduit 15, arm passage 90, chamber 20, sample chamber 30 and out the vent pipe 36. Because the solution 55 has a known concentration of alcohol in it, the concentration of the alcohol in the standard sample produced is known, and the reading of the IR detector can be immediately determined to be correct or incorrect. If it is incorrect, it can be recalibrated. If it is correct, the instrument is in proper condition for receiving a breath sample.

Before the breath sample is introduced, the purge and test cycles are repeated. The pump 42 is then turned off. The solenoid valves are preferably moved to the position shown in FIG. 6, at which the lines 46 and 52 are closed, and the breath sample is introduced through the breath inlet line 10.

It can be appreciated that the entire cycle can be controlled by a simple microprocessor computer, programmed to energize the various elements at the appropriate times in response to predetermined criteria.

The system thus provides assurance through the purge, test and blank steps, that a proper base line, blank test and calibration of the IR system have been established. The system thus provides reliable evidence in any judicial proceeding.

Numerous variations in the construction of the apparatus and in the method of this invention within the scope of the appended claims will become apparent to those skilled in the art in the light of the foregoing disclosure.

I claim:

1. Apparatus for analyzing the alcohol content of breath comprising an inlet line; an inlet line check valve in said inlet line; a sample inlet conduit communicating with the output side of said inlet line check valve; an alcohol detector communicating with said sample inlet conduit; a test line communicating at one end with said inlet line on the inlet side of the inlet line check valve and at its other end with a 2-way suction valve in a pump suction line, said inlet valve being selectively movable between a position at which it completes a connection between said test line and said pump suction line and a position at which it completes a connection between said pump suction line and an atmosphere line; an air pump, the suction side of which communicates with said suction line; a pressure line communicating with the pressure side of said pump at one end and with a 2-way pressure valve at the other; said pressure valve being selectively movable between a position at which it communicates with a purge line communicating with the sample inlet conduit and a position at which it communicates with an alcohol standard pressure line; an alcohol standard solution container with a bubbler tube communicating with said alcohol standard pressure line; and an alcohol standard sample line communicating with said alcohol standard solution container at one end and with an inlet side of a sample line check valve at the other; the outlet side of said sample line check valve communicating with the said sample inlet conduit, and said purge line communicating with said sample inlet conduit between the said outlet side of the said sample line check valve and the outlet side of the breath inlet check valve.

* * * * *